(12) United States Patent
Hackney et al.

(10) Patent No.: US 9,730,784 B2
(45) Date of Patent: Aug. 15, 2017

(54) CONNECTIVE TISSUE REPAIR PAD

(75) Inventors: Roger Graham Hackney, Leeds (GB);
David John Beevers, Leeds (GB);
Lauren Tidball, Leeds (GB)

(73) Assignee: Xiros Limited (GB)

( * ) Notice: Subject to any disclaimer, the term of this patent is extended or adjusted under 35 U.S.C. 154(b) by 404 days.

(21) Appl. No.: 14/237,507

(22) PCT Filed: Jul. 20, 2012

(86) PCT No.: PCT/GB2012/051749
§ 371 (c)(1),
(2), (4) Date: Jul. 1, 2014

(87) PCT Pub. No.: WO2013/017836
PCT Pub. Date: Feb. 7, 2013

(65) Prior Publication Data
US 2014/0350675 A1    Nov. 27, 2014

(30) Foreign Application Priority Data

Aug. 2, 2011 (GB) .................................. 1113303.0

(51) Int. Cl.
*A61F 2/00* (2006.01)
*A61F 2/08* (2006.01)
(52) U.S. Cl.
CPC .............. *A61F 2/08* (2013.01); *A61F 2/0063* (2013.01); *A61F 2/0077* (2013.01);
(Continued)
(58) Field of Classification Search
CPC .................................. A61F 2/08; A61F 2/0063
See application file for complete search history.

(56) References Cited

U.S. PATENT DOCUMENTS

| 4,546,769 A | 10/1985 | Planck et al. |
| 4,839,215 A | 6/1989 | Starling et al. |

(Continued)

FOREIGN PATENT DOCUMENTS

| EP | 0 145 492 A2 | 6/1985 |
| EP | 0 744 162 A2 | 11/1996 |

(Continued)

OTHER PUBLICATIONS

Non-Final Office Action for U.S. Appl. No. 14/168,848, filed Jan. 30, 2014, and mailed from the USPTO Aug. 14, 2015, 16 pgs.

(Continued)

*Primary Examiner* — Katrina Stransky
*Assistant Examiner* — Wade P Schutte
(74) *Attorney, Agent, or Firm* — Stoel Rives LLP

(57) ABSTRACT

The invention relates to an implantable prosthetic device for the repair of connective tissue in an animal or a human. In one embodiment, an implantable prosthetic device (100) for the repair of connective tissue (500) in an animal or human is disclosed which comprises a biocompatible pad (101) having an open structure to provide a scaffold for the in-growth of tissue into the pad; and a reinforcement region (206) attached to or formed integrally with the pad. The device is arranged so that it can be attached to tissue by forming a puncture (301) either a) within the reinforcement region, or b) in an area of the pad which is inboard of the reinforcement region, so that a suture (300) can be located through the puncture, the reinforcement region serving to support tensile loading in the device during use by resisting pull-through of the suture.

21 Claims, 5 Drawing Sheets

(52) U.S. Cl.
CPC ............... *A61F 2002/0086* (2013.01); *A61F 2220/0008* (2013.01); *A61F 2220/0075* (2013.01)

(56) References Cited

U.S. PATENT DOCUMENTS

| | | | |
|---|---|---|---|
| 5,441,508 A * | 8/1995 | Gazielly | A61F 2/08 602/44 |
| 6,042,534 A * | 3/2000 | Gellman | A61F 2/0045 600/30 |
| 6,652,872 B2 | 11/2003 | Nevo et al. | |
| 2002/0052660 A1 | 5/2002 | Greenhalgh | |
| 2003/0023316 A1 | 1/2003 | Brown et al. | |
| 2003/0212462 A1* | 11/2003 | Gryska | A61F 2/0063 623/23.72 |
| 2004/0060410 A1 | 4/2004 | Leung et al. | |
| 2004/0133275 A1 | 7/2004 | Mansmann | |
| 2007/0041952 A1 | 2/2007 | Guilak et al. | |
| 2008/0207989 A1 | 8/2008 | Kaleta et al. | |
| 2008/0241213 A1 | 10/2008 | Chun et al. | |
| 2008/0243149 A1* | 10/2008 | Kockerling | A61F 2/0063 606/151 |
| 2009/0138082 A1 | 5/2009 | Reah et al. | |
| 2009/0156986 A1 | 6/2009 | Trenhaile | |
| 2010/0063599 A1* | 3/2010 | Brunelle | A61L 31/044 623/23.72 |
| 2010/0152530 A1 | 6/2010 | Timmer et al. | |
| 2010/0179591 A1 | 7/2010 | Saltzman et al. | |
| 2011/0082479 A1 | 4/2011 | Friedlander | |
| 2011/0118762 A1* | 5/2011 | Dooney, Jr. | A61B 17/0401 606/148 |
| 2011/0125287 A1 | 5/2011 | Hotter et al. | |
| 2012/0053399 A1 | 3/2012 | Rao et al. | |
| 2013/0116799 A1* | 5/2013 | Derwin | A61F 2/02 623/23.72 |

FOREIGN PATENT DOCUMENTS

| | | |
|---|---|---|
| EP | 1 537 883 A2 | 6/2005 |
| GB | 2 276 823 A | 10/1994 |
| GB | 2 342 865 A | 4/2000 |
| WO | WO 01/39694 A2 | 6/2001 |
| WO | WO 02/30324 A1 | 4/2002 |
| WO | WO 02/35990 A2 | 5/2002 |
| WO | WO 03/007847 A1 | 1/2003 |
| WO | WO 03/095609 A2 | 11/2003 |
| WO | WO 2008/100685 A2 | 8/2008 |
| WO | WO 2013/017835 A1 | 2/2013 |
| WO | WO 2013/017836 A2 | 2/2013 |

OTHER PUBLICATIONS

International Search Report and Written Opinion for PCT/GB2012/051749 filed Jul. 20, 2012, and mailed from the International Searching Authority on Feb. 7, 2013, 16 pgs.

International Preliminary Report on Patentability for PCT/GB2012/051749 filed Jul. 20, 2012, and mailed from the International Bureau on Feb. 13, 2014, 9 pgs.

"Entangle," Merriam-Webster.com, Merriam-Webster, n.d. Web. May 1, 2016 from http://www.merriam-webster.com/dictionary/entangle, 8 pgs.

Final Office Action for U.S. Appl. No. 14/168,848, filed Jan. 30, 2014, and mailed from the USPTO on May 20, 2016, 18 pgs.

Non-Final Office Action for U.S. Appl. No. 14/171,203, filed Feb. 3, 2014, and mailed from the USPTO on Mar. 6, 2017, 34 pgs.

Non-Final Office Action for U.S. Appl. No. 14/235,885, filed Apr. 28, 2014, and mailed from the USPTO on Nov. 30, 2016, 27 pgs.

* cited by examiner

CONNECTIVE TISSUE REPAIR PAD

CROSS-REFERENCE TO RELATED APPLICATIONS

This application is a national stage application under 35 U.S.C. §371 of International Application No. PCT/GB2012/051749, titled CONNECTIVE TISSUE REPAIR PAD, filed Jul. 20, 2012, which claims priority to Great Britain Application No. 1113303.0, filed Aug. 2, 2011, which is hereby incorporated by reference in its entirety.

The present invention relates to an implantable prosthetic device for the repair of connective tissue in an animal or a human.

Biological connective tissues are susceptible to tearing, for example when placed under excessive tensile forces. Such tearing is a common problem where a tendon or ligament has been weakened through excessive use as is common to sports professionals. Typical examples include Achilles tendon injuries and torn rotator cuff tendons.

Example devices for reconstruction of ligaments and tendons are disclosed in GB 2151487, U.S. Pat. No. 5,217,495, US 2004/0078089, U.S. Pat. No. 4,728,329, WO 2006/089267 and WO 2009/109778.

However, there is a continued need for improved connective repair devices that may be conveniently and securely anchored to connective biological tissue.

Accordingly, the inventors provide an implantable prosthetic patch or pad that may be secured to connective tissue using suitable anchorages, typically in the form of sutures. The present device may therefore be provided with eyelets or regions through which the anchorage cord may be threaded to securely attach the pad to the soft connective tissue.

In an aspect of the present invention, a prosthetic pad is provided which comprises a generally triangular configuration having a substantially straight edge base and domed or pointed region extending from the base. According to one aspect, the pad may be divided into a plurality of segments by seams. The seams are configured to be cut by a surgeon or other user to obtain a pad of the desired shape and geometry. The seams may be formed by cord, a higher weave, braid or knit density or by sutures. The seams may be formed from the same or a different material to a main body of the pad. According to a further aspect, the pad comprises reinforcement means at the straight edge or base region to allow the pad to be attached to the connective tissue via suitable anchorage cord, tape, pin, anchor or suture. Such means may comprise cord loops and/or a length of cord, suture, stitching or a region of greater weave, braid or knit density that may be punctured by a sharp instrument to provide an eyelet through which to thread the anchorage device.

According to a first aspect of the present invention there is provided an implantable prosthetic device for the repair of connective tissue in an animal or human, the device comprising:
  a biocompatible pad having an open structure to provide a scaffold for the in-growth of tissue into the pad; and
  a reinforcement region attached to or formed integrally with the pad;
  in which the device can be attached to tissue by forming a puncture:
    a) within the reinforcement region; or
    b) in an area of the pad which is inboard of the reinforcement region;
  so that a suture can be located through the puncture, the reinforcement region serving to support tensile loading in the device during use by resisting pull-through of the suture.

According to a second aspect of the present invention there is provided a kit for use in repairing connective tissue in an animal or human, the kit comprising:
  an implantable prosthetic device comprising a biocompatible pad having an open structure to provide a scaffold for the in-growth of tissue into the pad, and a reinforcement region attached to or formed integrally with the pad; and
  a suture for attaching the device to tissue;
  in which the device is attached to the tissue by forming a puncture:
    a) within the reinforcement region; or
    b) in an area of the pad which is inboard of the reinforcement region;
  so that the suture can be located through the puncture, the reinforcement region serving to support tensile loading in the device during use by resisting pull-through of the suture.

The biocompatible pad provides a scaffold which can lead to rapid in-growth, to facilitate repair of damaged connective tissue. However, the open structure of the pad is such that tensile loading on the pad during use, for example by a suture, may lead to pull-through of the suture (save perhaps in a situation where a relatively large number of sutures is employed, thereby spreading the load on the pad). This could result in damage to the pad. The reinforcement region counteracts the tendency for the suture to pull-through the pad by supporting this tensile loading. In particular, forming a puncture: within the reinforcement region itself; or in an area of the pad which is inboard of the reinforcement region, is such that contact between the suture and the reinforcement region resists pull-through of the suture and so damage to the pad.

Reference is made to the positioning of the puncture inboard of the reinforcement region. It will be understood that the puncture may be 'inboard' of the reinforcement region in that it is positioned further into the pad, taken in a direction from an edge or perimeter of the pad. The puncture may be inboard of the reinforcement region in that it is outside the reinforcement region and positioned so that the reinforcement region is located between the puncture and an adjacent edge of the pad. The adjacent edge of the pad which is referred to may be that which is closest to the puncture.

The puncture may be formed in the pad of the device during manufacture, or may be formed during a surgical procedure to implant the device.

Where the reinforcement region is attached to the pad, the reinforcement region may comprise an elongate reinforcement element, which may be a multi-filament or monofilament element. Suitable multi-filament elements include yarns and cords. The reinforcement element may be a suture. The reinforcement region may be formed by a single coil of suture, multiple coils of sutures where each pass is discrete, or multiple coils of the same suture. The reinforcement region may comprise at least one anchoring element for anchoring the reinforcement element to the pad. The anchoring element may be a multi-filament or monofilament element. Suitable multi-filament elements include yarns, cords or sutures. The anchoring element may pass through the pad in a first direction, around the reinforcement element and back through the pad in a second direction which is opposite to said first direction, to anchor the reinforcement element to the pad. The anchoring element may make multiple passes through the pad and around the reinforcement element. This may form a number of loops extending around the reinforcement element. The reinforcement region may comprise a first anchoring element and a second anchoring element. At least one of the anchoring elements may be attached to the pad before the reinforcement element, and so positioned between a surface of the pad and the reinforcement element. A spacing between loops of the first anchoring element may be different to a spacing between loops of the second anchoring element. The or each anchoring element may be embroidered or stitched to the pad so that it extends around the reinforcement element. The first and second anchoring elements may be stitched or embroidered to the pad and a stitch pattern of the first anchoring element may be different to a stitch pattern of the second anchoring element.

Where the reinforcement region is formed integrally with the pad, the reinforcement region may be of a density which is greater than a remainder of the pad. In other words, the pad may have a greater number of fibres (or material forming the pad) per unit volume in the reinforcement region than in a remainder of the pad. Providing a pad having such a reinforcement region may resist pull-through of the suture in that it may provide a greater resistance to applied tensile loading than a remainder of the pad.

At least part of the reinforcement region may extend substantially parallel to at least one edge of the pad. At least part of the reinforcement region may be positioned within the perimeter of the pad, and may be positioned inboard of an edge or edges of the pad. At least part of the reinforcement region may be positioned adjacent to at least one edge of the pad. The reinforcement region may comprise a part which extends substantially parallel to one edge of the pad, and at least one further part which extends substantially parallel to another edge of the pad. The reinforcement region may extend around a perimeter of the pad, parts of the reinforcement region extending substantially parallel to the respective pad edges.

Said reinforcement region may be a primary reinforcement region, and the device may comprise at least one secondary reinforcement region. The secondary reinforcement region may be attached to or formed integrally with the pad, and may be attached to or formed with the primary reinforcement region. Where the primary reinforcement region extends around a perimeter of the pad, the secondary reinforcement region may extend between a part of the primary reinforcement region which extends parallel to and/or is positioned adjacent to a first edge of the pad, and a part of the primary reinforcement region which extends parallel to and/or is positioned adjacent to a further edge of the pad. The secondary reinforcement region may extend in a length direction of the pad. The secondary reinforcement region may extend in a direction which is transverse to a length direction of the pad. The secondary reinforcement region may extend in a width direction of the pad, which may be perpendicular to a length direction of the pad. The pad may comprise at least two secondary reinforcement regions, at least one of said regions crossing at least one other.

According to a third aspect of the present invention there is provided an implantable prosthetic device for the repair of connective tissue in an animal or human, the device comprising: a biocompatible pad having an open structure to provide a scaffold for the in-growth of tissue into the pad; a cord attached to the pad, the cord having a (first) bent or curved section that defines at least partially an eyelet capable of receiving an anchorage suture (such as a cord) to attach the pad to the tissue.

According to a fourth aspect of the present invention there is provided an implantable prosthetic device for the repair of connective tissue in an animal or human, the device comprising: a biocompatible pad having an open structure to provide a scaffold for the in-growth of tissue into the pad; a reinforcement region attached to or formed integrally with the pad, the reinforcement region capable of being punctured to form an eyelet receiving an anchorage suture (such as a cord) to attach the pad to the tissue.

The following further features may apply to one or more of the devices defined above.

The cord or reinforcement region may be positioned and/or attached towards a perimeter region of the pad. The reinforcement may be a suture that extends over a straight edge base region of the pad. The suture may be substantially linear or may comprise curved or bent regions. The reinforcement suture may extend over the base region of the pad and/or the perimeter may comprise looped sections that extend beyond the perimeter of the pad.

The pad may comprise a biocompatible fibre based material. The pad may be a needle-punched material (or felt). The pad may therefore comprise entangled fibres and may have an open or low fibre density structure to facilitate tissue ingrowth into the pad. Alternatively the pad or patch may comprise a textile material such as a woven or non-woven material including a knitted or braid-based structure. Where the pad is woven the density of the mesh weave and/or the weave pattern may be different at different regions of the pad to affect the physical/mechanical properties and/or the degree of tissue ingrowth once implanted.

Accordingly, the present device may be configured for biological fixation post implantation as tissue grows into the pad to replace the initial mechanical anchorage achieved through the attachment of the pad to the connective tissue via the suture/anchorages that are looped through the device.

Where the reinforcement regions comprise a suture such as a cord, the cord may be attached to the pad by stitching.

The bent and/or curved regions of the suture (cord) may at least partially define eyelets that are closed loops in that the suture (cord) is bent back on itself so as to overlap or contact itself. Alternatively, the eyelets are formed by at least one bent or the curved section of suture (cord) that defines is an open loop such that the suture (cord) does not completely bend back on itself and does not overlap, touch or cross.

The pad may be formed as a single layer of material.

The device may comprise regions of the pad that are reinforced relative to a main part of the pad. These reinforced regions may be configured to receive the suture/anchorage cord to attach the device to the connective tissue. In particular where the pad or patch is woven the reinforcement regions may comprise regions of greater weave density that may be punctured by a surgeon to thread and attached the suture/anchorage cord to the patch and then thread this cord into the connective tissue. Such devices would not necessarily comprise the bent or curved regions of cord to define eyelets.

The patch may be woven or non-woven and the reinforcement regions may be woven or non-woven regions and may be formed from cord, stitching or at least one suture.

In the kit of the second aspect of the invention, the suture used to attach the device to tissue may be pre-attached or pre-coupled to the pad, and so the kit supplied with a preformed puncture or punctures, and the suture: located in the puncture, attached to the pad by the reinforcement element; or integral to the primary reinforcement. The device would then be attached to tissue by passing a free end or ends of the suture into the tissue in a conventional manner; or the pre-attached suture formed into a loop or loops through which an attachment suture or the like can be located to attach the device to tissue. The suture may however be supplied as an individual or separate item together with the device. The latter approach may be preferable, as this would provide a surgeon the ability to place the suture(s) in a position considered to be appropriate at the time that the surgical procedure to implant the device is carried out.

According to a fifth aspect of the present invention, there is provided a method of repairing connective tissue, the method comprising the steps of:

positioning a biocompatible pad of an implantable prosthetic device relative to a first biological tissue site, the pad having an open structure to provide a scaffold for the in-growth of tissue into the pad and a reinforcement region attached to or formed integrally with the pad;

forming a puncture:
  a) within the reinforcement region; or
  b) in an area of the pad which is inboard of the reinforcement region;

attaching the device to the first tissue site using a suture which passes through the tissue and the puncture, so that the reinforcement region can support tensile loading in the device during use by resisting pull-through of the suture; and attaching the device to a second biological tissue site such that the device forms a bridge between the first and second tissue sites.

According to a sixth aspect of the present invention, there is provided a method of repairing connective tissue, the method comprising the steps of:

positioning a biocompatible pad of an implantable prosthetic device relative to a first biological tissue site, the pad having an open structure to provide a scaffold for the in-growth of tissue into the pad and a cord attached to the pad, the cord having a bent or curved section which at least partially defines an eyelet;

attaching the device to the first tissue site by passing a suture through the tissue and through the eyelet; and attaching the device to a second biological tissue site such that the device forms a bridge between the first and second tissue sites.

Further features of the methods may be derived from the text above relating to the first to fourth aspects of the invention.

According to a seventh aspect of the present invention there is provided a method of repairing connective tissue comprising: securing to a first biological tissue site, the device as described here comprising: a biocompatible pad or patch and a cord and/or reinforcement material, the pad being attached to the first tissue site using at least one anchorage; and attaching the device to a second biological tissue site using a second anchorage such that the pad or patch forms a bridge between the first and second biological tissue sites.

Embodiments of the present invention will now be described by way of example only and with reference to the accompanying drawings in which.

Figure 11:
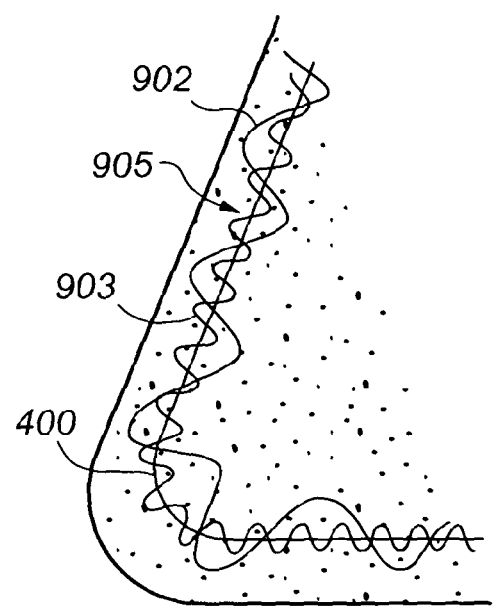
Figure 12:
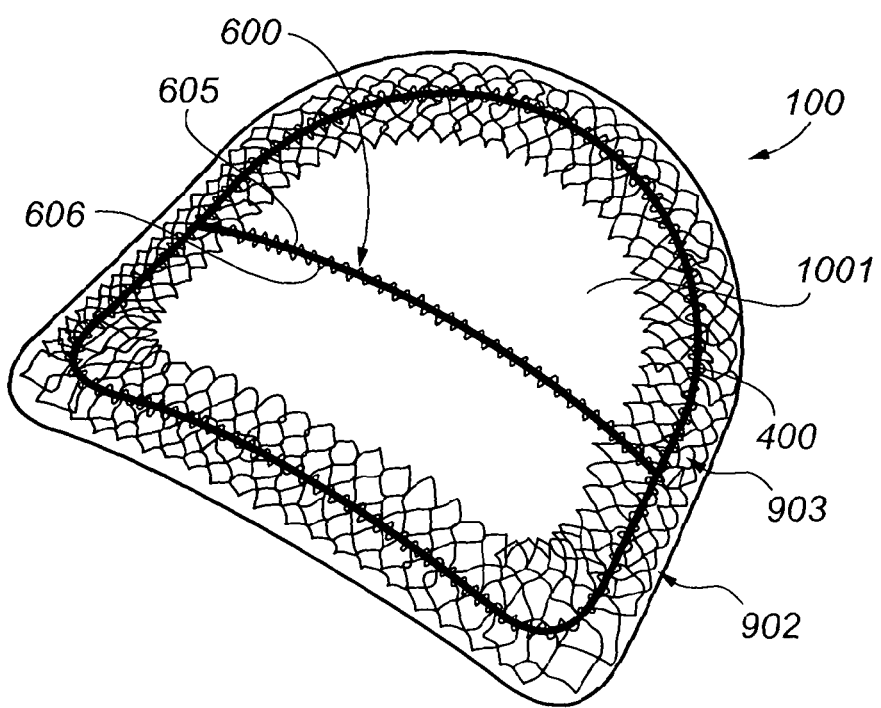

FIG. 11 is a plan view of part of an implantable prosthetic device for the repair of connective tissue in accordance with a further embodiment of the invention, illustrating a further method of attaching a reinforcement region to a pad of the device; and FIG. 12 is a plan view of an implantable prosthetic device for the repair of connective tissue in accordance with a further embodiment of the invention.

Figure 1:
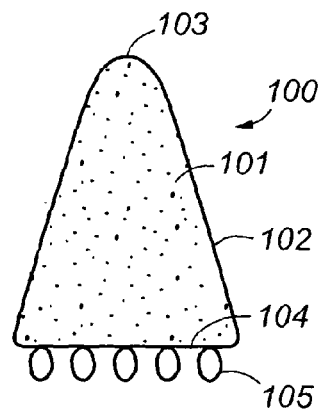
FIG. 1 is a plan view of an implantable prosthetic device for the repair of connective tissue comprising a generally triangular pad and looped eyelet regions according to an embodiment of the invention.

Referring to FIG. 1, an implantable prosthetic device 100 is shown which comprises a pad 101 formed from fibres or cord. Pad 101 is substantially triangular having a straight edge base 104 from which a main body of the pad 101 extends, terminating at an opposite end in a generally rounded dome 103. According to the specific embodiment, a perimeter region of pad 102 is not reinforced. However, according to further embodiments the perimeter 102 may be reinforced by additional reinforcement material such as cord stitching, a suture or a change in the density of the material of pad 101.

Figure 5:
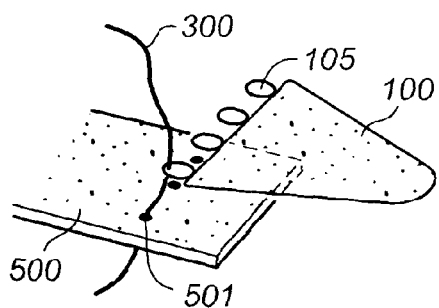
FIG. 5 is a perspective view of the pad of FIG. 1 positioned for attachment to a torn rotator cuff.

Attachment loops 105 extend from edge 104 beyond the pad perimeter 102. Loops 105 are closed-loops and are formed from a suture attached to the base edge region 104. The suture may be a suitable attachment cord. Loops 105 may be formed from a single suture or may be formed from individual sutures. Referring to FIG. 5, the eyelets 105 are configured to receive at least one anchorage cord or tape (suture) 300 to attach the device 100 to connective tissue 500. Cord 300 is threaded through each loop 105 and pulled tight to attach securely the device 100 at an upper or lower face of tissue 500 by threading cord 300 through tissue 501.

Figure 2:
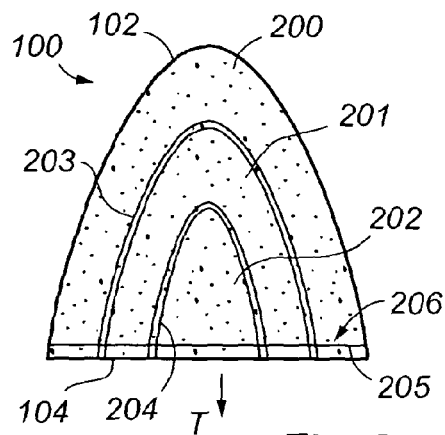
FIG. 2 is a plan view of a repair patch divided into segments by a plurality of seams such that the pad may be cut to change the size and geometry according to another embodiment of the invention.

FIG. 2 illustrates a further embodiment of the device 100 of FIG. 1, incorporating a pad which differs to the pad 101 of FIG. 1. In this embodiment, the pad has a plurality of concentric segments 200, 201, 202 defined in part by a plurality of intermediate seems 203, 204. As with FIG. 1, the general shape of the device of FIG. 2 is substantially triangular. However, the pad of FIG. 2 does not include the eyelets 105 of the pad 101 shown in FIG. 1. Outer segment 200 is defined by outer perimeter edge 102 and a first seam 203 formed from parallel aligned sutures or suitable cord. A second inner seam 204 defines the inner edge of intermediate segment 201 and the outer edge of innermost segment 202. The base of each segment 200, 201, 202 is defined, in part, by the straight edge 104 of the triangular pad 100. A reinforcement region 206 is provided by a suture 205 which extends parallel to edge 104 and within the perimeter of the pad 102. As will be described below, the suture 205 is secured to the pad segments 200, 201, 202 such as by stitching, braiding or embroidering so that the suture 205 and the stitching forms the reinforcement region 206.

In use, a surgeon may cut along (or adjacent to) each seam 203, 204 to achieve the desired shape and configuration of pad 100. The device may then be secured to the connective tissue 500 by threading an anchorage cord (not shown) through the pad segments 200, 201 and 202. Specifically, the pad segments 200, 201, 202 are punctured such as by a needle carrying the anchorage cord. The punctures (not shown) in the pad segments 200, 201, 202 are formed inboard of the reinforcement region 206, that is further into the pad in a direction from the edge 104. The punctures are thus in an area of the pad which is outside the reinforcement region 206, and positioned so that the reinforcement region 206 is located between the puncture and the adjacent edge 104 of the pad. In this way, tensile loading in the pad (acting in the direction of the arrow T), which would otherwise cause pull-through of the anchorage cord, is resisted by the reinforcement region. In particular, the tensile loading is resisted by the suture 205, which distributes the load across a wider area of the pad, by means of the multiple contact points provided by stitching the suture to the pad.

In a variation on the embodiment of FIG. 2, loops similar to the loops 105 shown in FIG. 1 may be passed through punctures in the pad inboard of the reinforcement 205, or loops 105 may be integral to the reinforcement 205, and the device 100 attached to tissue by passing a separate suture or the like through the loops 105, as described above in relation to FIG. 1.

Figure 3:
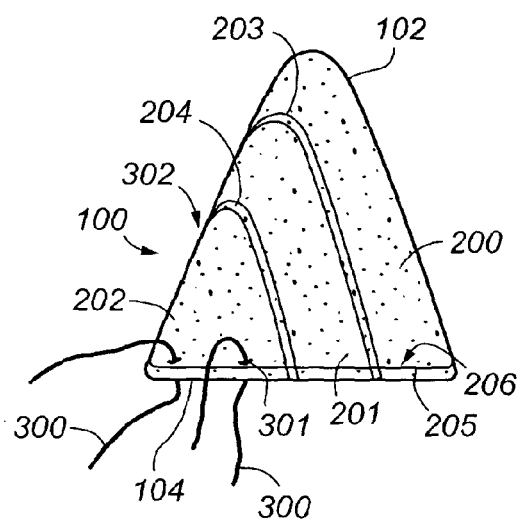
FIG. 3 is a plan view of a further embodiment of the pad of FIG. 2.

FIG. 3 illustrates a further embodiment of the segmented pad of FIG. 2. According to this embodiment, one edge of each domed segment 200, 201, 202 are aligned so as to be a common edge such that the segments 200, 201, 202 are not concentric. This reduces the seam length with respect to the embodiment of FIG. 2. As illustrated, and in use, the pad segments 200, 201 and 202 are punctured at 301. Only the punctures 301 in the segment 202 are shown. It will be understood that the number of punctures which are formed will depend upon the shape of the pad, in particular if the pad is cut as described above, to change its dimensions. Again, the punctures 301 are formed in an area of the pad which is inboard of edge 104, and so outside the reinforcement region 206, and positioned so that the reinforcement region 206 is located between the puncture 301 and the adjacent edge 104 of the pad. A surgical cord 300 is threaded through the punctures 301 in the pad segments 200, 201 and 202. The cord 300 may be considered to be positioned immediately behind (or inboard of) the innermost edge of base reinforcing suture 205, and is looped around the suture 205. It will be understood that these loops may be formed from a continuous length of suture or from separate sutures.

Figure 4:
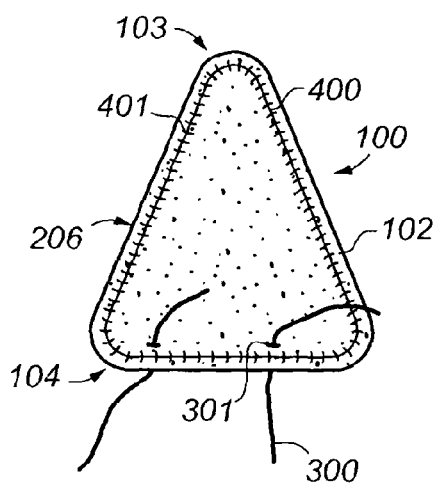
FIG. 4 is a plan view of an implantable prosthetic device for the repair of connective tissue in accordance with a further embodiment of the invention.

FIG. 4 illustrates a further embodiment of the device of FIG. 1, again without attachment eyelets 105. According to the further embodiment, a reinforcement region 206 is formed which comprises a suture 400 that extends around the entire perimeter of the generally triangular pad. Suture 400 is secure in position by suitable seam stitching 401 or other mechanical attachment means (such as or embroidering). Suture 400 sits just within the perimeter 102 of pad 100. Again, and as illustrated in FIG. 3, the suture 400 provides reinforcement of the pad such that the anchorage cords 300 may be looped inboard of the suture 400 immediately inside edge 104 to provide secure attachment. That is, suture 400 is configured to bear the tensile loading forces when the pad is implanted. Again, the stitching 401 serves to distribute the loading imparted on the suture 400 across a wider region of the pad, to thereby resist pull-through of the surgical cord 300 used to anchor the pad.

Figure 6:
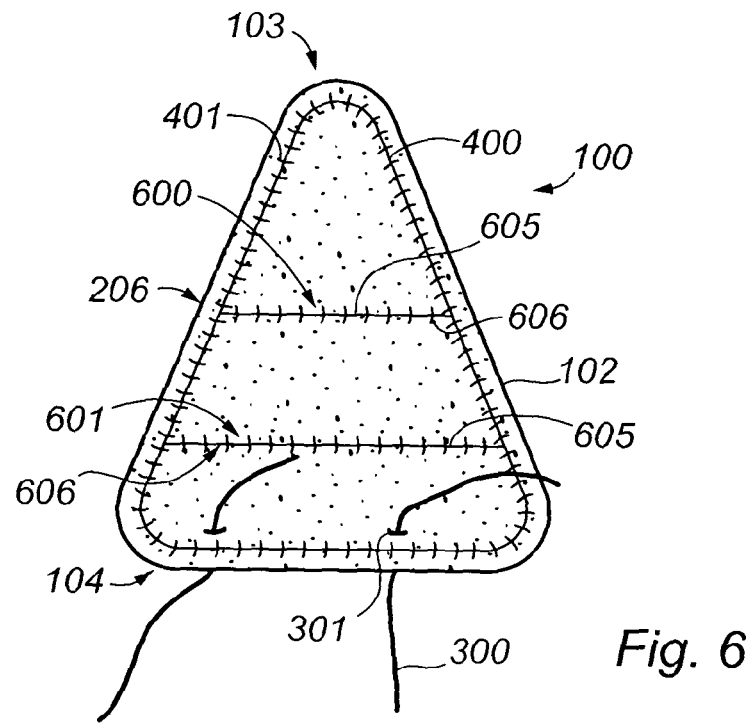
FIG. 6 is a plan view of an implantable prosthetic device for the repair of connective tissue in accordance with a further embodiment of the invention.

FIG. 6 illustrates a further embodiment of the device of FIG. 4 where additional reinforcement 600 and 601 is provided. The suture 400 and associated stitching 401 then forms a primary reinforcement region 206, whilst the reinforcements 600 and 601 form or provide a secondary reinforcement. By way of illustration, two horizontal reinforcements 600 and 601 are shown, although fewer or more can be used. These extend in a width direction of the device 100, that is perpendicular to its main, length direction. The reinforcements 600, 601 each comprise sutures 605 which are secured by stitching 606 or other mechanical attachment means (such as braiding or embroidering). The reinforcements 600, 601 limit or prevent stretch in the direction of reinforcement.

Figure 7:
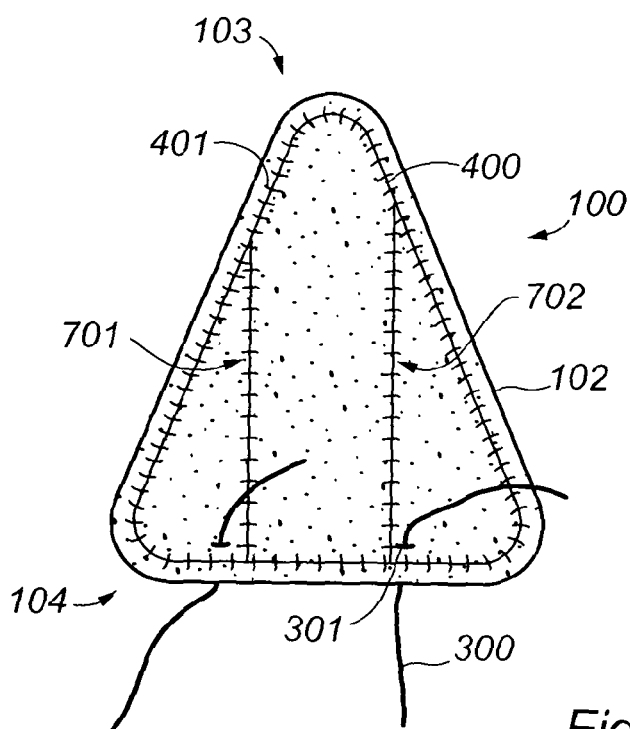
FIG. 7 is a plan view of an implantable prosthetic device for the repair of connective tissue in accordance with a further embodiment of the invention.

FIG. 7 illustrates a further embodiment of the device of FIG. 4 where additional (secondary) reinforcement 701 and 702, is provided, in this case extending in an alternative direction. As can be seen, the reinforcement 701, 702 extends in the main, length direction of the device 100.

The secondary reinforcement may be provided by a single or series of separate links, or the reinforcements may be continuous with each other and separate to the perimeter reinforcement, or the reinforcements may be integral to the perimeter reinforcement. Where such multiple reinforcements 600, 601 and/or 701, 702 are employed, it will be understood that they are not limited to being parallel, nor is each reinforcement limited to being straight, as shown.

Figure 8:
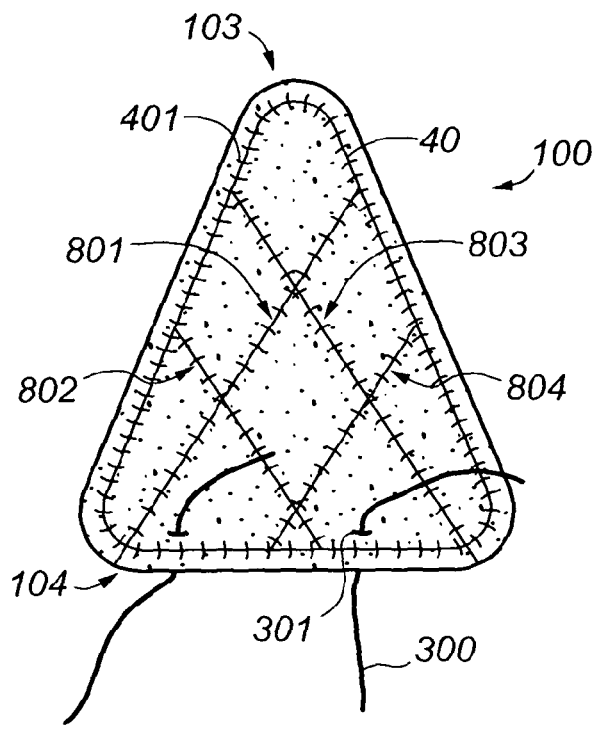
FIG. 8 is a plan view of an implantable prosthetic device for the repair of connective tissue in accordance with a further embodiment of the invention.

FIG. 8 illustrates a further embodiment of the device of FIG. 4 where additional (secondary) reinforcement is provided which extends in multiple directions 801, 802. In this example, the reinforcement 801, 802 is 'cross hatched', so that the reinforcements cross one another.

Figure 9:
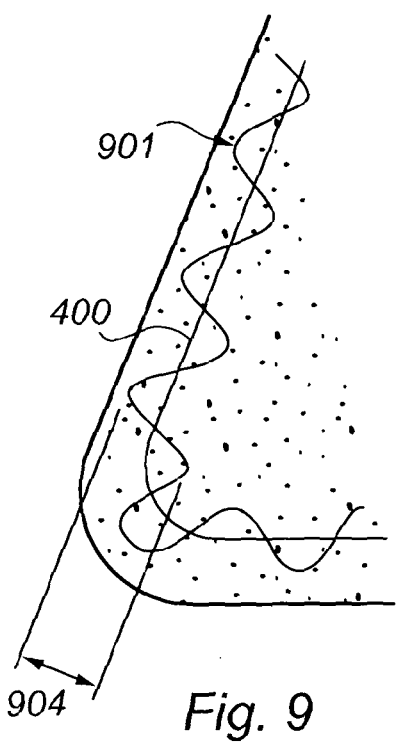
FIG. 9 is a plan view of part of an implantable prosthetic device for the repair of connective tissue in accordance with a further embodiment of the invention, illustrating a method of attaching a reinforcement region to a pad of the device.
Figure 10:
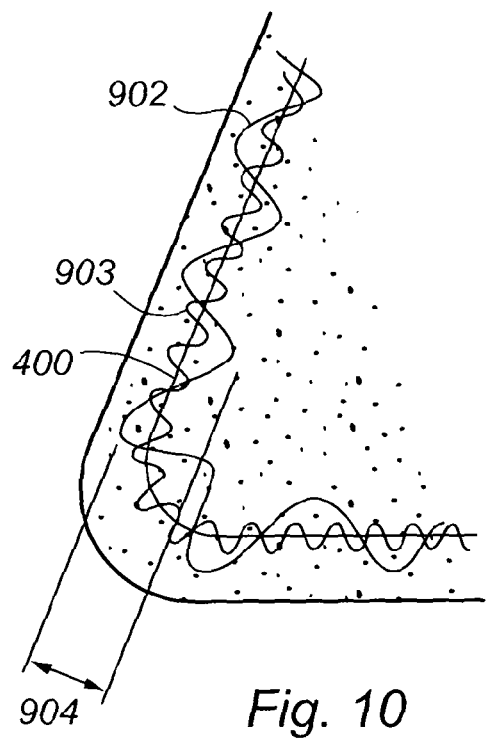
FIG. 10 is a plan view of part of an implantable prosthetic device for the repair of connective tissue in accordance with a further embodiment of the invention, illustrating another method of attaching a reinforcement region to a pad of the device.

FIGS. 9 and 10 illustrate variations on the device of FIG. 4, where the method of joining the reinforcement to the pad is a single cord, suture, yarn, or fibre 901 (FIG. 9); or multiple cords, sutures, yarns, or fibres 902 and 903 (FIG. 10). The fibres 902 and 903 have different stitching patterns to provide different support for the reinforcement suture 400. In this way, a distance between loops of the stitches 902 is greater than between loops of the stitches 903. In each case, the fibres 901, 902 and 903 have multiple stitches, nodes or contact points with the pad, by which the transition of loads between the reinforcement 400 and the pad is spread over a wide area 904. The cord or cords may also be designed to transfer a greater proportion of load the closer they are placed to the reinforcement. By way of example, the stitches 903 provided closer/adjacent to the reinforcement suture 400 may have a denser pattern, such as is shown at 905 in FIG. 11.

Turning now to FIG. 12, there is shown a further embodiment of the device 100 of FIG. 1, incorporating a pad 1001 which differs to the pad 101 of FIG. 1. In this embodiment, the pad 1001 is knitted, but may be woven, non-woven or otherwise formed. The primary reinforcement 400 is secured to the pad 1001 by means of first and/or second fibres 902 and 903. In this embodiment, the first fibres 902 are formed into a pattern which further distributes the loads between the reinforcement suture 400 and the pad 1001, the pattern formed by embroidery. A secondary, horizontal reinforcement or cross member 600 comprising a suture 605 is secured by stitching 606. This horizontal suture 605 may be a separate component, or preferably an extension of the reinforcement suture 400.

In more detail, where the pad 1001 is knitted, it will typically be warp knitted, but may be weft knitted if desired. The primary reinforcement suture 400 is passed three times around the perimeter in a continuous fashion. It is also passed three times for the secondary cross member 605, which is continuous with the perimeter reinforcement 400. In this way, all the reinforcements come from a single suture. This suture is attached to the pad 1001 using the sutures 902 and/or 903, which are separate and of thinner diameter. Again only one thin suture is used and this is continuous. In this way, all the reinforcement region components 400, 902 and 903 are from single sutures. An embroidery machine is used to create the pattern of the sutures 902 and 903. This includes relatively tight, closely packed stitches of the suture 903, 606 (which go directly over the reinforcement thick suture elements 400 and 605, and so both the perimeter and cross member), and the more widely spaced diamond type pattern for the suture 903.

In a particular construction method, the diamond shaped pattern of the suture 902 is first embroidered on the pad 1001 using the thinner diameter suture, which is one continuous suture. Then the reinforcement suture 400 (which is thicker) is laid down in a configuration which means it passes around the perimeter, and the cross member 605, at least three times, all continuously. Then the thinner suture 903 is used to 'overstitch' and hold the reinforcement suture 400 in place, again as a continuous suture.

In the embodiments described above, the punctures are generally formed inboard of the reinforcement region of the relevant pad. This provides the advantage that movement of an anchorage cord or suture through the material of the relevant pad will cause the cord to come into contact with an edge zone of the reinforcement region, so that further movement of the cord will be resisted by the reinforcement region across its entire width. However, the punctures may be formed within the reinforcement region. For example, in the embodiment of FIG. 9, the puncture may be formed within the area 904 itself, such as between the loops of the cord loops 901.

The devices described above can be used in the repair of biological connective tissues, particularly those which have torn, for example when placed under excessive tensile forces. Typical examples include repair of achilles tendon injuries and torn rotator cuff tendons. The devices are attached to tissue at both ends. The tissue may be bone at one end and soft tissue such as that of the ligament to be repaired at the other, or soft tissue at both ends. For example, a lower (viewing the figures) portion of the patch may be attached to bone. A surgeon may place, for example, three sutures through the bone and then attach these sutures to the lower edge of the device patch. The surgeon would then use many sutures, placed throughout the edge of the non-reinforced region of the pad (such as in the dome-shaped region above (in the figures) the lower reinforced region), to locate the patch to the soft tissue. The surgeon can place many sutures to stabilise the soft tissue, which share the load, so that there is less need for reinforcement. However, placing many sutures is time consuming, and management of so many sutures is tricky. Therefore it may be preferred to provide the reinforcement extending around the entire perimeter (or a greater proportion of the perimeter) of the pad, particularly where it is to be used as a repair device for the rotator cuff. In this way, fewer sutures can be used to secure the patch to the soft tissue.

Also, in the embodiments described above, a kit may be provided comprising the relevant device plus a suture (or other anchorage device or element) for attaching the device to tissue. The suture used to attach the device to tissue may be pre-attached or pre-coupled to the pad, or the suture attached to the pad by the reinforcement element, or the suture being integral to the primary reinforcement. The device would then be attached to tissue by passing a free end or ends of the suture into the tissue in a conventional manner. The suture may be supplied as an individual or separate item with the device. The latter approach may be preferable, as this would provide a surgeon the ability to place the sutures in a position considered to be appropriate at the time that the surgical procedure to implant the device is carried out.

Various modifications may be made to the foregoing without departing from the spirit or scope of the present invention.

For example, references are made herein to a cord or cords, which will be understood to be multi-filament structures. It will be understood however that other structures, such as mono-filament structures (e.g. wire) may be employed, where appropriate.

The invention claimed is:

1. An implantable prosthetic device for the repair of connective tissue in an animal or human, the device comprising:
   a biocompatible pad having an open structure to provide a scaffold for the in-growth of tissue into the pad; and
   a reinforcement region attached to the pad and reinforcing a portion of the pad relative to a main portion of the pad, the reinforcement region being positioned inboard of an edge or edges of the pad and extending around a perimeter of the pad, the reinforcement region comprising an elongate reinforcement element, and a first anchoring element and a second anchoring element for anchoring the reinforcement element to the pad;
   in which one of the first and second anchoring elements is attached to the pad before the reinforcement element and so positioned between a surface of the pad and the reinforcement element, and in which the other one of the first and second anchoring elements passes through the pad in a first direction, around the reinforcement element and back through the pad in a second direction which is opposite to said first direction, to anchor the reinforcement element to the pad;
   and in which the device is attachable to tissue by forming a puncture:
   a) within the reinforcement region; or b) in an area of the pad which is inboard of the reinforcement region;
   the puncture adapted to receive a suture, the reinforcement region serving to support tensile loading in the device during use by resisting pull-through of the suture.

2. A device as claimed in claim 1, in which the reinforcement element is anchored to the pad around the entire perimeter by the at least one anchoring element.

3. A device as claimed in claim 1, in which a spacing between loops of the first anchoring element is different to a spacing between loops of the second anchoring element.

4. A device as claimed in claim 1, in which the reinforcement region is formed by a single coil of suture, multiple coils of sutures where each pass is discrete, or multiple coils of the same suture.

5. A device as claimed in claim 1, in which at least part of the reinforcement region extends substantially parallel to at least one edge of the pad and is positioned adjacent to said edge.

6. A device as claimed in claim 1, in which the reinforcement region comprises a part which extends substantially parallel to one edge of the pad, and at least one further part which extends substantially parallel to another edge of the pad.

7. A device as claimed in claim 1, in which parts of the reinforcement region extend substantially parallel to the respective pad edges.

8. A device as claimed in claim 1, in which said reinforcement region is a primary reinforcement region, and the device comprises at least one secondary reinforcement region attached to or formed integrally with the pad.

9. A device as claimed in claim 8, in which the primary reinforcement region extends around the perimeter of the pad, parts of the reinforcement region extending substantially parallel to the respective pad edges, and in which the secondary reinforcement region extends between a part of the primary reinforcement region which extends parallel to a first edge of the pad, and a part of the primary reinforcement region which extends parallel to a further edge of the pad.

10. A device as claimed in claim 8, in which the device comprises at least two secondary reinforcement regions, at least one of said regions crossing at least one other.

11. A device as claimed in claim 1, in which the pad has a substantially straight edged base and a domed or pointed region extending from the base.

12. A device as claimed in claim 1, in which the pad is divided into a plurality of segments by one or more seams, said seams configured to be cut to obtain a pad of the desired shape and geometry.

13. A device as claimed in claim 12, in which said seams are formed by cord, a higher weave, braid or knit density or by sutures.

14. A device as claimed in claim 1, in which the reinforcement region comprises a suture which extends over a straight edged base region of the pad.

15. A device as claimed in claim 14, in which the suture comprises curved or bent regions.

16. A device as claimed in claim 14, in which the suture is attached to the pad by stitching.

17. A device as claimed in claim 1, in which the reinforcement element forms at least one loop which defines an eyelet for receiving a separate suture for attaching the device to tissue.

18. A device as claimed in claim 1, in which the pad comprises a surface, and in which the elongate reinforcement element is positioned on the surface of the pad and secured to the surface by the at least one anchoring element.

19. A device as claimed in claim 18, in which the entire elongate reinforcement element rests on the surface of the pad.

20. A device as claimed in claim 1, in which the reinforcement region is provided adjacent a perimeter of the pad, and in which at least part of a remainder of the pad is free from reinforcement.

21. A device as claimed in claim 8, in which the device comprises at least two secondary reinforcement regions attached to or formed integrally with the pad, at least one of said regions crossing at least one other.

* * * * *